United States Patent [19]

Melsky

[11] Patent Number: 4,973,319
[45] Date of Patent: Nov. 27, 1990

[54] SLIT VALVE MEDICAL CATHETER

[75] Inventor: Gerald S. Melsky, Lexington, Mass.

[73] Assignee: Therex Corp., Walpole, Mass.

[21] Appl. No.: 349,719

[22] Filed: May 10, 1989

[51] Int. Cl.$^5$ .......................................... A61M 25/00
[52] U.S. Cl. ..................................... 604/247; 137/860
[58] Field of Search .................. 604/247, 280, 264, 9; 137/860, 853

[56] References Cited

U.S. PATENT DOCUMENTS 4,657,536 4/1987 Dorman ............................. 604/247
4,701,166 10/1987 Groshong et al. .................. 604/247

FOREIGN PATENT DOCUMENTS 727959 4/1955 United Kingdom ................ 604/247

Primary Examiner—Stephen C. Pellegrino
Attorney, Agent, or Firm—Nutter, McClennen & Fish

[57] ABSTRACT

A slit valve medical catheter includes a flexible tube the distal end of which is closed. A length of resilient tubing is mounted coaxially to the distal end segment of the tube so that the tubing extends along the inside or outside surface of the tube. The tubing is slitted lengthwise and an aperture is formed in the tube wall directly opposite each slit with the aperture being wider than the slit so that portions of the tubing wall on opposite sides of each slit overhang the sides of the corresponding aperture.

13 Claims, 1 Drawing Sheet

SLIT VALVE MEDICAL CATHETER

This invention relates to a medical catheter. It relates more particularly to an in-dwelling medical catheter with an improved slit valve construction to prevent retrograde fluid flow into the catheter.

BACKGROUND OF THE INVENTION

Medical catheters are used for the intravenous administration of therapeutic agents or nutrients. A catheter is inserted into the body through an incision into a moderately sized vein using an introducer and is threaded along the vein into a large vein such as the superior vena cava. Because of the large blood flow through that cavity, a concentrated infusate solution delivered through the catheter is rapidly diluted thus allowing the administration of a high concentration of therapeutic agent or nutrient.

Since the catheter is in-dwelling in the patient's body for a relatively long period, provision is made for preventing retrograde flow of blood or other body fluids into the catheter. Usually this is accomplished by providing a one-way valve at the distal end of the catheter. In many applications, the preferred type of valve is a so-called slit valve, an example of which is described in U.S. Pat. No. 4,327,722.

Basically, a slit valve is a one-way valve formed by one or more slits cut into the catheter wall near the distal end of the catheter. When the fluid pressure inside the catheter is greater than the fluid pressure outside the catheter by a selected amount, the opening defined by the slit expands. When the pressure outside the catheter is greater than the inside pressure, the valve opening will close and prevent fluid flow into the proximal end of the catheter. The pressure differential needed to open the valve may vary from catheter to catheter in accordance with the number of slits in the catheter, the length of the slits, the thickness of the catheter wall or the elasticity of the catheter wall.

In practice, the formation of a slit valve in the end of a catheter is a very exacting process. The edges of the slit must be shaped very precisely if the valve is to perform as intended, namely, to open only when the pressure inside the catheter exceeds the outside pressure by a predetermined amount. Also, in some applications, the desirable characteristics for the catheter per se are antagonistic to the proper operation of the valve in the catheter. For example, in a given case, the proper operation of the slit valve may call for a catheter wall which is thin and catheter wall material which is very soft and flexible. However, catheters made of such soft and flexible materials are difficult to insert into and thread along the patient's veins or other blood vessels to the selected infusion site. To facilitate the insertion of such catheters, ancillary wires or other stiffening means have been incorporated into the catheters; see U.S. Pat. No. 4,559,046, for example. Obviously the inclusion of such stiffening devices increases the overall cost of the catheter. Moreover, those devices must be removed after the catheter is inserted thereby complicating the insertion process as a whole.

Also, in some cases it is desirable to withdraw blood or other fluids from the body through an implanted catheter. While it is usually possible to cause a slit valve to open by creating a lower fluid pressure inside the catheter than outside, in practice it is generally not possible to withdraw fluids through a conventional catheter with a slit valve because the catheter, being soft and thin-walled tends to collapse and close off if the internal fluid pressure is lowered.

Finally, many catheters in use today are connected to implanted vascular access ports. In such use, the catheter must be connected securely and reliably to the access port. Making such a connection is difficult if soft thin-walled catheter tubing must be used.

SUMMARY OF THE INVENTION

Accordingly, it is an object of the present invention to provide an improved slit valve medical catheter.

Another object of the invention is to provide a catheter of this type which is relatively easy and inexpensive to manufacture as compared to prior slit valve catheters.

A further object of the invention is to provide a slit valve medical catheter whose valve properties are substantially independent of the material of which the catheter tube is made.

Yet another object of the invention is to provide a slit valve catheter which can be inserted readily into the body without requiring ancillary means to stiffen the catheter.

Another object of the invention is to provide a slit valve catheter which can be used to withdraw as well as infuse fluids.

Still another object of the invention is to provide a slit valve catheter which can be attached easily to an implantable vascular access port.

Other objects will, in part, be obvious and will, in part, appear hereinafter. The invention accordingly comprises the features of construction, combination of elements and arrangement of parts which will be exemplified in the following detailed description, and the scope of the invention will be indicated in the claims.

Briefly, our slit valve catheter includes the usual flexible catheter tube having a closed distal end and a conventional connector or coupling fitted integrally to the proximal end of the catheter tube. There is also a slit valve structure located adjacent to the distal end of the catheter tube. However, instead of being formed integrally with the catheter tube, the slit valve structure comprises a second flexible tube which is snugly fitted coaxially to the distal end segment of the catheter tube.

In other words, that second tube may surround the distal end segment of the catheter tube or that distal end segment of the catheter tube may surround the second tube. In either event, one or more axial or lengthwise slits are formed in the wall of the second tube each of which functions as a valve. Also, an aperture is formed in the distal end segment of the catheter tube wall directly opposite each of the slits in the second tube. These apertures are sufficiently larger than the slits that they provide enough clearance to allow the slit walls to flex during operation of the valves. Also, when a particular slit valve is open, the aperture opposite that valve does not materially effect fluid flow through that valve.

Using the construction described herein, a one-way or check valve can be provided adjacent to the distal end of the catheter which will permit fluid flow at the distal end of the catheter only when the fluid pressure inside the catheter exceeds the fluid pressure outside the distal end of the catheter by a predetermined amount. Also, if a particular application calls for it, the catheter may be provided with a valve characteristic which permits retrograde flow into the distal end of the catheter when the external pressure there exceeds the pressure inside the catheter by a selected amount. In fact, as we shall see, it is even possible to design the valve such that it permits forward fluid flow through the catheter when the fluid pressure inside the catheter exceeds the outside fluid pressure by a selected value and permits retrograde flow through the catheter when the outside fluid pressure exceeds the inside pressure by a selected amount, which amount may be the same as or different from the first amount.

It is also a feature of this invention that whatever the characteristics of the slit valve, those characteristics are substantially independent of the material of which the catheter tube is made. In other words, the catheter tube may be made of a relatively stiff material to facilitate its insertion into the patient and/or its connection to an implanted vascular access port without materially affecting the operation of the valve or valves at the distal end of the catheter.

The tubular components of our catheter can be made of conventional implant grade catheter tubing such as of silicone rubber or other suitable material which can be cut in a conventional manner to form the slits and apertures at the distal end of the catheter, but without the preciseness needed to form the integral slits in prior slit valve catheters. Therefore, the overall cost of our catheter should be less than the costs of conventional medical catheters with a valving capability.

In those cases in which it is desirable for the sleeve in which the slits are formed to have a very thin wall, such a thin-walled structure is easily manufactured by dip-casting. To make a sleeve by dip casting, a mandrel whose outer diameter is equal to the desired inner diameter of the sleeve is dipped into a dispersion of silicone rubber compound in a solvent such as toluene. When the mandrel is removed, it is found to be coated with a very thin layer of dispersion which will cure to a very thin sleeve as the solvent evaporates. The wall thickness of the sleeve will be very uniform and may be controlled by repeated dipping or by adjusting the viscosity of the dispersion through the addition or deletion of solvent. Once cured, the sleeve is most easily removed from the mandrel by swelling the silicone sleeve via immersion in trichlorotrifluoroethane. Once swollen the sleeve is easily slipped off the mandrel and slid onto the distal and segment of the catheter tube. Upon evaporation of the swelling agent, the sleeve will resume its original shape and close down achieving a shrink fit around the catheter tube. Once in place, the sleeve can be bonded to the catheter tube, if needed, and slit by any appropriate means.

BRIEF DESCRIPTION OF THE DRAWING

For a fuller understanding of the nature and objects of the invention, reference should be had of the following detailed description, taken in connection with the accompanying drawing, in which.

DESCRIPTION OF THE PREFERRED EMBODIMENTS

Figure 1:
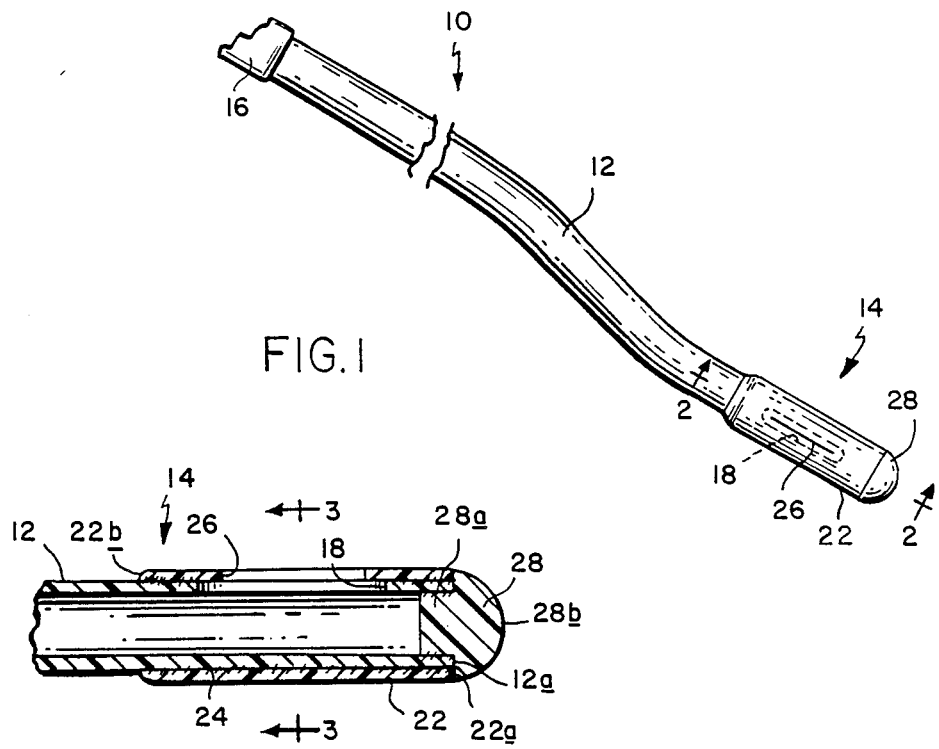
FIG. 1 is a fragmentary isometric view of a slit valve medical catheter made in accordance with this invention.

Referring to FIG. 1 of the drawing, our catheter shown generally at 10 includes a flexible catheter tube 12 made of medical grade silicon rubber or other similar material. Present at the distal segment end of catheter tube 12 is a slit valve structure shown generally at 14. The opposite or proximal end of tube 12 is terminated by a conventional coupling 16 of a type that is commonly used on medical catheters of this type. The coupling connects to a mating fitting at the end of a tube extending from a source of infusate as shown in FIG. 1, or it can be connected to the outlet of an implantable port such as the one disclosed in application Ser. No. 343,914, filed Apr. 26, 1989, for example, the contents of which is incorporated herein by reference.

Figure 2:
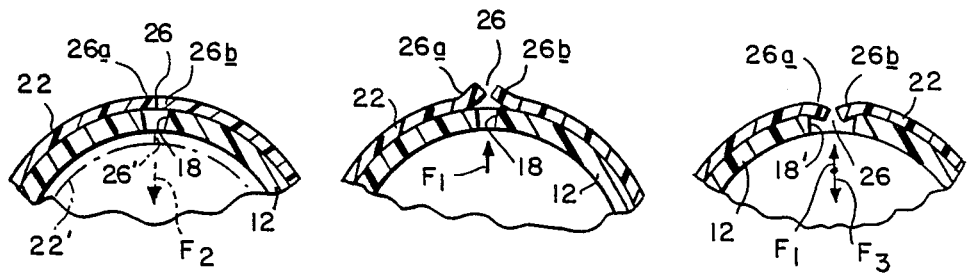
FIG. 2 is a fragmentary sectional view taken along line 2—2 of FIG. 1 showing the check valve component of the FIG. 1 catheter in greater detail.

Referring now to FIGS. 1 and 2, formed in the wall of tube 12 adjacent to its distal end 12a is one or more lengthwise openings or apertures 18. Each aperture is in the order of 2 to 10 mm long and 1 to 5 mm wide and if there is more than one such aperture, they should be spaced around the circumference of tube 12 so as not to unduly weaken the distal end segment of the catheter.

The valve structure 14 comprises, in addition to tube 12, a relatively short length of tubing 22 that snugly surrounds the distal end segment of the catheter tube 12. Tubing 22 is preferably also made of a medical grade catheter material which may be the same as, or different from, the material of tube 12 depending upon the particular application. In fact, tubing 22 can be a short length of conventional catheter tubing whose inside diameter is comparable to the outside diameter of tube 12. Alternatively, and particularly if a thin wall is desired, it may be made by the dip casting process described above. This will provide a very uniform thin walled sleeve which will form a valve which operates reliably at very low actuation pressure so that it is easy to introduce blood into a blood vessel, for example. Tubing 22 is slid over the end segment of catheter tube 12 as shown in FIG. 2 so that its distal end 22a is flush with the catheter tube end 12a. Preferably, a suitable bonding agent or adhesive film 24 is present between tubing 22 and tube 12 to firmly bond the tube and tubing together and to provide a fluid-tight seal between those two members. Preferably also the proximal end 22b of tubing 22 is rounded or beveled to provide a relatively gradual and smooth transition between the tube and tubing exterior surfaces at that location.

Still referring to FIG. 2, tubing 22 is formed with a lengthwise slit 26 opposite each one of the apertures 18 in tube 12, the ends of each slit lying inboard the opposite ends of the corresponding aperture 18. The length of each slit (when closed) may be in the range of 1 to 9 mm depending on the desired valve characteristics.

The distal end of tube 12 is closed and the distal end of catheter 10 as a whole is finished off by a closure member 28. The illustrated member 28 has a reduced diameter stem 28a which plugs tightly into the tube end 12a with the surface of member 28 forming a rounded or tapered nose 28b that is flush with the outer surface of tubing 22 so that there are no sharp edges or projections present at the distal end of the catheter 10. Desirably, the closure member 28 is secured in place by adhesive 24 applied to the opposing surface of member 28 and the tube and tubing exterior surfaces so that a fluid-tight seal is present at the distal end of the catheter 10.

Figures 3, 3A, 4:
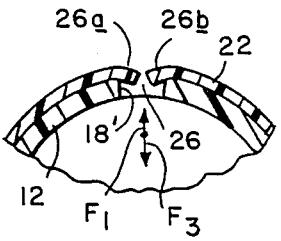
FIGS. 3 and 3A are sectional views taken along line 3—3 of FIG. 2 on a much larger scale showing the FIG. 2 valve in its closed and open positions, respectively.
FIG. 4 is a view similar to FIG. 3 illustrating a valve capable of two-way flow at different inside/outside pressure differentials.

As best seen in FIGS. 2 and 3, the width of the aperture 18 opposite each slit 26 in tubing 22 is such that the wall segments 26a and 26b on each side of a slit 26 overhang the side walls of the corresponding aperture 18 to some extent. The extent of the overhang varies depending upon the particular application. The illustrated valve structure 14 is intended to provide a one-way forward flow through the distal end of the catheter only when the fluid pressure inside that end of the catheter exceeds the pressure outside that end of the catheter by a predetermined amount, e.g. about ½ psi. For this particular application, then, the width of each aperture 18 should be in the order of 3 mm.

When the wall of tubing 22 opposite each aperture 18 is in its normal relaxed state, the opposite walls 26a and 26b of each slit 26 abut one another as shown in FIG. 3 so that there is essentially no opening through tubing 22 at that location. This is the situation that prevails when the internal and external hydrostatic pressures at the distal end of the catheter 10 are the same. However, when the fluid pressure inside catheter 10 exceeds the outside pressure by a predetermined amount, the net force spreads apart the walls 26a and 26b of each slit as shown in FIG. 3A allowing fluid to flow from inside catheter tubing 12 through the aperture 18 in the tube wall and out through the open slit 26 as indicated by the arrow $F_1$ in FIG. 3A. When that pressure differential drops or disappears, the slit walls 26a and 26b resume their unstressed natural state shown in FIG. 3 thereby closing the slit 26 and stopping the flow of fluid through the catheter.

The pressure at which the valve structure 14 will open depends primarily on the elasticity of the tubing 22 material, the thickness of the tubing 22 wall and the length of each slit 26. Retrograde fluid flow into the catheter through the valve structure 14 at the pressure differential normally encountered by the catheter is inhibited because the slit walls 26a and 26b are supported from within by the walls of the tube aperture 18. In other words, the tube 12 material around each aperture 18 provides internal support for the wall of tubing 22 around each slit 26 thereby preventing the tubing material around the slit from folding or spreading apart inwardly to the extent that the slit 26 opens inwardly. In effect then, the tube 12 material present inside tubing 22 stiffens, or increases the resistance to opening of, the slit 26 by an inward deflection of the slit walls 26a and 26b, but does not affect the ability of the slit walls to open or spread apart due to an outward deflection of those walls.

This two-ply valve structure 14 thus provides an effective one-way valve at the distal end of catheter 10 without having to provide a slit 26 that is precisely cut with specially beveled or shaped edges or walls to achieve the desired one-way flow through the catheter. On the contrary, an effective valve structure is created with each slit 26 being formed by a simple cut at right angles through the tubing 22 wall as shown in the drawing figures.

Also, since the valving action is accomplished primarily by the tubing 22, the material of which tubing 22 is made can be selected solely on the basis of its valving function. By the same token, since the catheter tube 12 does not contribute significantly to the operation of the valve structure 14, the tube material can be selected on the basis of characteristics such as lubricity and stiffness that make it easy to insert the catheter 10 into a patient's body and/or to connect the catheter to a source of infusate such as an implanted vascular access port.

The illustrated catheter 10 has a valve structure 14 which permits only fluid outflow. In some applications, it may be desirable for the catheter to permit only fluid inflow, i.e. to permit flow into the distal end of the catheter only when the fluid pressure inside the distal end of the catheter is less than the fluid pressure outside by a predetermined amount. Such an arrangement could be used, for example, to enable the physician to draw a negative pressure in the catheter and thereby suck blood or other body fluid out of the patient's body through the catheter. An arrangement such as this is shown in phantom in FIG. 3. There, the slit valve-forming tubing 22' is fit snugly inside the distal end segment of the catheter tube 12. Tubing 22' is provided with at least one lengthwise slit 26' which is disposed opposite the aperture 18 in the tube 12 wall.

Normally, each slit 26' is closed as shown in FIG. 3 due to the natural resilience of the tubing material. However, when the fluid pressure outside the distal end of the catheter exceeds the fluid pressure inside the catheter due, for example, to a vacuum being drawn in the catheter, the side edges or walls of each slit 26' will spread apart and open inwardly allowing fluid to flow into the catheter as indicated by the phantom arrow $F_2$ in FIG. 3. Fluid flow in the forward direction is prevented by the presence of the aperture walls 18a which overlie and stiffen the sides of each slit preventing the slit walls from opening outward at the pressure differentials normally encountered by the catheter. Since the valving action does not depend on catheter tube 12, that tube can be relatively stiff so that it will not collapse when fluid is withdrawn through the catheter.

In many specific applications, it is desirable to have two-way fluid flow through the catheter valve structure 14. For example, one may want to administer a therapeutic agent to the patient through catheter 10 without any danger of retrograde flow under normal circumstances, but also to withdraw blood from the patient through the catheter under special circumstances. The catheter valve structure depicted in FIG. 4 permits such two-way flow under different internal/external fluid pressure conditions. The valve structure in the FIG. 4 catheter includes a tube 12 formed with an aperture 18' which is wider than the aperture 18 of the one-way valve structure 14 described above. The widening of the aperture 18' in this fashion reduces the support provided by tube 12 at the side walls 26a and 26b of each slit 26. Resultantly, whereas an outward flow $F_1$ will result when the fluid pressure inside the catheter exceeds the pressure outside the catheter distal end by a predetermined first amount, fluid inflow $F_3$ will occur when the fluid pressure outside the catheter exceeds the inside fluid pressure by a selected second amount that is greater than the pressure differential causing fluid outflow.

It will be seen from the foregoing, then, that the medical catheter construction disclosed herein facilitates the making of such catheters with a valving capability in that the characteristics of the valve can be made substantially independent of the material of which the catheter tube is made. Thus the catheter tube can be made of a material which facilitates the introduction of the catheter into the desired vein or other blood vessel in a patient's body and/or the connection of the catheter to an infusate source. On the other hand, the tubing 22 material comprising the valve structure 14 can be made as thin as needed and otherwise selected to obtain the desired operating characteristics for the valve so that specifically shaped end cut slits are no longer required. Since the material selection and slitting processes are simplified, the cost of this catheter should be less than that of prior slit valve catheters. Accordingly, the catheter described herein should find wide application wherever the intravenous administration or withdrawal of fluids is practiced.

It will thus be seen that the objects set forth above among those made apparent from the preceding description are efficiently attained and, since certain changes may be made in the above constructions without departing from the scope of the invention, it is intended that all matter contained in the above description or shown in the accompanying drawing shall be interpreted as illustrative and not in a limiting sense. It is also to be understood that the following claims are intended to cover all of the generic and specific features of the invention herein described.

I claim:

1. A medical catheter comprising a flexible tube made of medical grade material, said tube having a proximal end, a distal end and a cylindrical wall extending between said ends; a length of resilient tubing mounted to said tube and extending along a relatively short distal end segment thereof; means defining at least one normally closed lengthwise slit in said tubing intermediate the ends thereof; means defining an aperture in said tube wall directly opposite and surrounding each said slit, each said aperture being wider than its corresponding slit so that tubing wall portions on opposite sides of the slit overhang the opposite edges of the associated aperture, and closure means for closing the distal end of said tube.

2. The catheter defined in claim 1 and further including means for establishing a fluid-tight seal between the opposing walls of said tube and tubing.

3. The catheter defined in claim 2 and further including coupling means affixed to the proximal end of said tube, said coupling means being in fluid communication with the tube interior.

4. The catheter defined in claim 3 wherein said coupling means is coupled to the outlet of a vascular access port.

5. The catheter defined in claim 2 wherein said tubing encircles said tube distal end segment.

6. The catheter defined in claim 2 wherein said tube distal end segment encircles said tubing.

7. The catheter defined in claim 2 wherein said tube is made of a stiffer material than the tubing.

8. The catheter defined in claim 7 wherein said tubing is made of soft silicone rubber and said tube is made of a relatively stiff silicone rubber.

9. The catheter defined in claim 2 wherein said tube wall is thicker than the wall of said tubing.

10. The catheter defined in claim 2 wherein said closure means forms a rounded or tapered nose at the distal end of said catheter.

11. The catheter defined in claim 2 wherein said tubing is a shrink wrap.

12. The catheter defined in claim 2 wherein said tubing is a casting.

13. The catheter defined in claim 2 wherein the opposing walls of the tube and tubing are bonded together.

* * * * *